United States Patent [19]

Burruss, Jr.

[11] 4,303,083
[45] Dec. 1, 1981

[54] DEVICE FOR EVAPORATION AND INHALATION OF VOLATILE COMPOUNDS AND MEDICATIONS

[76] Inventor: Robert P. Burruss, Jr., 6433 79th St., Cabin John, Md. 20731

[21] Appl. No.: 196,058

[22] Filed: Oct. 10, 1980

[51] Int. Cl.³ .......................... A24F 5/00; A24F 5/04
[52] U.S. Cl. .................................. 131/271; 131/330;
   131/194; 131/195; 131/198 R
[58] Field of Search ............. 131/270, 271, 273, 330, 131/193, 194, 195, 196, 198 R, 198 A; 128/203.27

[56] References Cited

U.S. PATENT DOCUMENTS 1,967,367  7/1934  Miele .............................. 131/198 A
2,104,266  1/1938  McCormick ....................... 131/330
4,141,369  2/1979  Burruss ............................ 131/330

Primary Examiner—V. Millin

[57] ABSTRACT

A device for inhaling a mixture of air and vaporized volatile compounds, but without combustion or thermal decomposition of the volatile compounds or of other non-volatile organic matter, as is the case in ordinary smoking methods. The device is intended to be handheld in a manner similar to that of an ordinary tobacco pipe. It can be used further to administer volatile medications, by route of the respiratory organs, to the bodily system of the user of the device. The device is intended to not achieve uncomfortable surface temperatures while at the same time it will be able to readily and rapidly evaporate compounds and mixtures of such compounds that can achieve a vapor pressure of one atmosphere at temperatures of less than 250° C.

1 Claim, 8 Drawing Figures

DEVICE FOR EVAPORATION AND INHALATION OF VOLATILE COMPOUNDS AND MEDICATIONS

This invention relates to a noncombustion and nonpyrolytic method for evaporating and inhaling the active volatile compounds and components of tobacco and of other smoking materials, and volatile medications, through controlled volatilization and evaporation into an airstream that can be inhaled in a manner homologous with ordinary tobacco smoking methods. The volatilization and evaporation is effected by the application of heat to the volatile compounds, examples of which are listed below, so that the volatile compounds can be evaporated and volatilized with a minimum amount of the high-temperature thermal decomposition and pyrolysis processes that generate the toxic and carcinogenic compounds found in the smoke of ordinary combustion-based methods of use of smoking materials.

The term "smoking materials" is intended to include any combustible organic materials containing volatile ingredients that the user desires to be inhaled into his mouth and lungs. Such materials include tobacco, licorice, eucalyptus, teas, flower petals, and other herbs.

The term "volatile compounds" is intended to include all volatile constituents or combinations of volatile constituents, or even individual purified volatile constituents that have a vapor pressure of one atmosphere at some temperature less than 250° C. and that can be extracted from smoking materials by combinations of heating and distillation or by solvent extraction methods. Examples include nicotine and other tobacco flavor ingredients, caffiene, and fragrant aromatic compounds extracted from spices. The term "volatile compounds" is also taken here to include an volatile synthetic or natural medication that has a vapor pressure of one atmosphere at a temperature of less than 250° C. and which also includes such medications as might be synthesized for use against such diseases as asthma, or other medications that might most efficaciously be absorbed into the bodily system of the user by way of the respiratory organs. Examples include epinepherine, in the case of an asthma sufferer, and anti-emetic, in the case of a cancer patient seeking relief from the emetic side effects of chemotherapeutic cancer treatment methods.

Prior art methods that use tobacco extracts and other volatile compounds and natural and synthetic flavor substances include those covered by U.S. Pat. Nos. 2,764,154 and 2,809,634. However, these inventions operate at room temperature and do not use any power sources with which to heat the volatile compounds, which constrains the use of these inventions to only the most volatile ingredients—i.e., to those extracts and volatile compounds having significant vapor pressures at room temperature, which does not include nicotine, for example, whioh is the primary flavor ingredient in tobacco smoke and which has a boiling temperature in excess of 100° C.

Other prior art methods of evaporating volatile substances into an airstream to be inhaled include those covered by U.S. Pat. Nos. 1,771,366 and 3,200,819. The device of U.S. Pat. No. 1,771,366 uses preheated air to evaporate a volatile medication from a "tampon" through which the heated air is drawn, and the design is such that the amount of heat that would be necessary to evaporate the volatile compounds that can be evaporated in the present invention would render the instrument of U.S. Pat. No. 1,771,366 far too hot to handle or to put to one's mouth.

The device of U.S. Pat. No. 3,200,819 is intended to look like and simulate a cigarette and relies on room-temperature evaporation of volatile substances contained in a "cartridge"; the mixture of air and evaporated substance to be inhaled is then heated, but only for the purpose of simulating the heat of an ordinary cigarette.

Both devices covered by U.S. Pat. Nos. 1,771,366 and 3,200,819 are complex compared to the present invention in which the volatile compounds to be evaporated are put into direct contact with a "heated surface" from which the compounds are readily and rapidly evaporated and simultaneously captured in an airstream that is thence inhaled. This process is carried out without undue temperature rise of the external surfaces that come in direct contact with the hands and mouth of the user.

One other prior art approach for the evaporation of volatile substances is covered by U.S. Pat. No. 3,431,393. This approach appears capable in design of evaporating volatile substances at the temperatures achieved by the present invention, but the device of U.S. Pat. No. 3,431,393 evaporates the substances into the free air with no provision for direct inhalation, and it cannot be easily or conviently held in the hand.

SUMMARY OF THE INVENTION

With the aforementioned considerations in mind, the present invention provides a method for the noncombustion and nonpyrolytic vaporization, into an airstream to be inhaled, of volatile compounds as defined above. Such method includes a main structural body, which may resemble an ordinary tobacco-smoking pipe, including a cavity therein corresponding to the "bowl" of an ordinary tobacco-smoking pipe, and which can be hand-held; a heat-generating electrical resistance element, said heat-generating element being supported inside the cavity of the main structural body but out of direct contact with the walls of the cavity; a heated surface in direct thermal contact with said heat-generating element and onto or into which the volatile compounds or mixtures of compounds can be placed for subsequent vaporization; a system of air passages so arranged that the evaporated volatile compounds can be entrained into an airstream that can be inhaled by the user of the device. The device would also include electrical power cord and an "on-off" switch, plus an indicator light to indicate unambiguously whether or not the power is in the "on", or active, mode. A thermostatic control element, and a manually-operated power modulation system can also be incorporated.

Suitable electrical heating elements include wire-wound resistors, carbon resistors, and resistance wire that is wound onto or embedded directly into the heated surface from which the volatile compounds are evaporated.

The volatile compound is applied to the heated surface by means of a squeeze tube, eye dropper, syringe, or application rod in amounts of several to tens of milligrams at a time. The volatile compounds are then vaporized, even at the rate of boiling, during which time air is drawn over the evaporating or boiling compound and the resultant mixture of air and evaporated compounds is inhaled into the mouth and respiratory passages of the user.

With adequate thermal isolation of the resistance heating element and the heated surface from the walls and surfaces of the main structural body, the power requirement can be reduced to a level of only 2 watts or less so that electrical power can be supplied by portable batteries that can be incorporated into the main structural body in an aesthetically-appealing way, or electrical power can be taken from home, office, and automobile electrical outlets.

By utilizing the approach of the present invention, a compact, efficient and rapidly-responding method is provided wherein the desired volatile compounds can be entrained in an air volume that is thence inhaled, and this can be done without the toxic hazards associated with ordinary smoking methods.

DETAILED DESCRIPTION OF THE DRAWINGS

Figure 1:
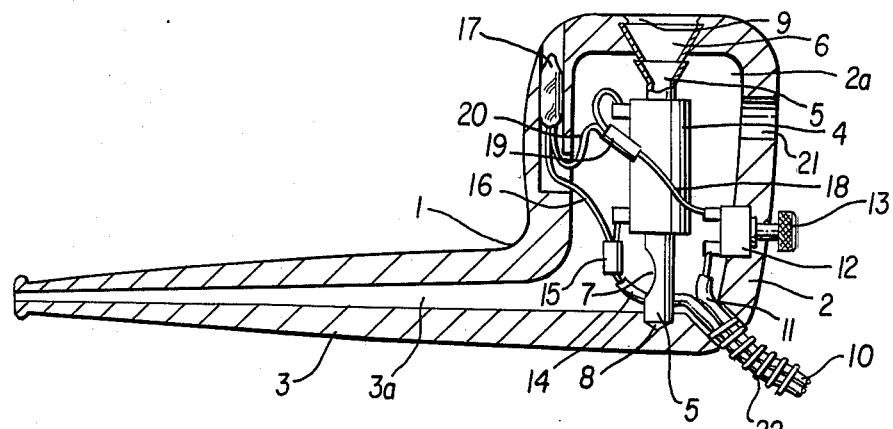
FIG. 1 is a cross-sectional view of one form of the present invention in which the heat-generating electrical resistance element is a vertically-mounted wire-wound electrical resistor, and the heated surface is a metal tube inserted axially through a bore in the resistor.
Figure 2:
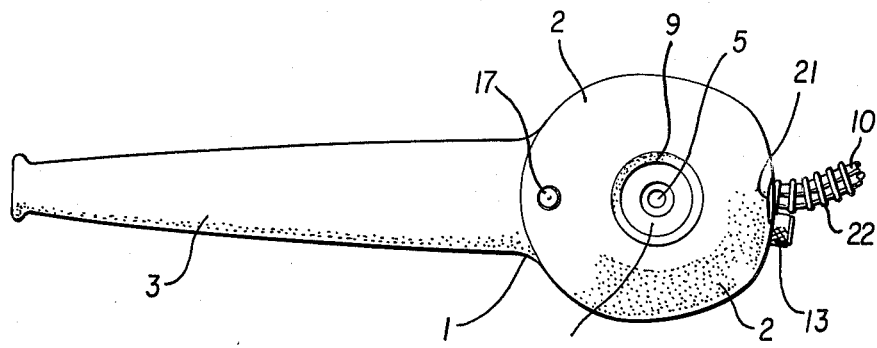
FIG. 2 is a top view of the arrangement shown in FIG. 1.

Referring now to FIGS. 1 and 2, there is shown a device, designated generally by the numeral 1, that can be used for evaporating the volatile compounds in such a way that the user of the device can inhale a mixture of air and evaporated volatile compounds, but without the generation of the toxic and dangerous combustion by-products associated with traditional smoking methods. Since the volatile compounds that are to be used in this device are merely evaporated in the device shown in FIG. 1 and in the variations shown in the subsequent figures, no combustion-related or pyrolytic-related products are generated.

The device 1 comprises a main structural body, designated by the numeral 2, having a cavity 2a, and including contiguous with its structure a stem and mouthpiece portion designated generally by the numeral 3 containing air passage 3a. The material of the main structural body 2, including the stem and mouthpiece portion 3, can be wood, plastic, or some other suitable and aesthetically-pleasing material, or some combination of such materials.

The resistance heating element 4 consists of a wire-wound resistor having a central bore with its axis oriented vertically in FIG. 1; and passing through the bore, and concentric with the bore is a surface to be heated that is metal tube 5. Metal tube 5 is made of brass, copper or aluminum. The metal tube 5 is flared at the upper end in order to connect with the base of the entrance funnel 6 which is made of a thin-walled material of relatively low thermal conductivity such as steel, stainless steel, or glass or some other ceramic material. The entrance funnel 6 receives the volatile compound in liquid form and directs its flow into the heated surface 5. The lower end of tube 5, where it protrudes from the body of the resistance heating element 4, has a portion of its circumference cut away at location 7 in such a way that air drawn into the device 1 by means of the mouthpiece and stem assembly 3 will pass downwards through the funnel 6 and into the heated tube 5, where the volatile compound is evaporated, and outwards at the port 7 in the tube 5 and thence into the stem and mouthpiece assembly 3 through which the user inhales.

Tube 5, especially in the heated region that is surrounded by the resistance heating element 4, constitutes the heated surface from which from which the volatile extract is evaporated after the volatile compound has been applied in liquid form to the entrance funnel 6. Tube 5 is supported in the main body 2 by being, at its lower end, at rest in a conical-shaped identation 8 in the bottom of the cavity in the main structural body 2, while at the top of tube 5 the flared portion rests against the small end of funnel 6 which itself fits with its larger uppermost end against the concentric lip 9 of the top of the entrance to the cavity 2a of the main structural body 2. The wire-wound resistance heating element 4, which is concentric with tube 5, is supported in place by having a snug fit on tube 5.

In addition to the above-mentioned components, the main structural body 2 has an aperature through which pass the electrical power leads 10, one lead of which, 11, connects with a combination on-off switch and variable rheostat or thermostat 12, that can be manipulated by means of knurled knob 13. The other electrical lead 14 connects by means of connector 15 with one of the wire leads that is permanently affixed to the electrical resistance heating element 4 and with a lead 16 that connects with the indicator lamp 17 which emits light when the device is in the "on" mode. The output wire 18 from the combination on-off switch and power control unit 12 connects also with the lead from the resistance heating element 4 by means of connector 19 and with the remaining wire 20 attached to the indicator lamp 17.

Vent hole 21 is bored through the main structural body 2, more or less horizontally, into the cavity 2a. The user of the device 1, by using a finger to variably occlude vent hole 21 can adjust the ratio of the volume of air passing close to heated surface 5, which contains the evaporating volatile compounds, to the volume of fresh air entering through vent hole 21, and can thereby modulate the temperature and concentration of the mixture of air and volatile compounds that are inhaled.

The electrical power leads 10 are protected from fatigue failure that can result from repeated flexure of the wire 10 at the place where it enters the main structural body 2 by means of a strain-relieving grommet, shown in FIG. 1 as a spring 22 that is coiled around the wire for an extent of about an inch from the outer surface of the main structural body 2.

Figure 3:
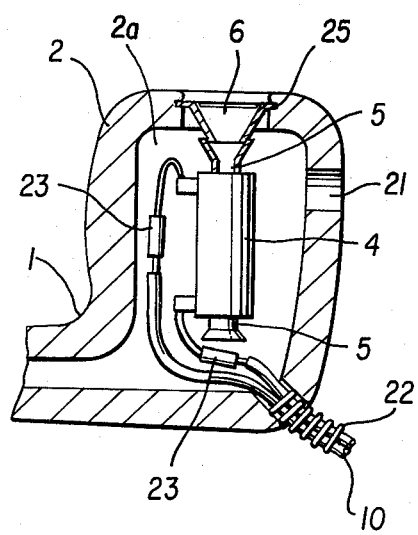
FIG. 3 is a cross-sectional view of another form of this invention; in this version the heated surface from which the volatile compounds are evaporated is also a metal tube extending downward through an axial hole in a vertically-mounted wire-wound electrical resistor, said tube being attached to and supported at the top opening to the cavity of the main structural body by a funnel-shaped conical element that connects to the main structural body.
Figure 4:
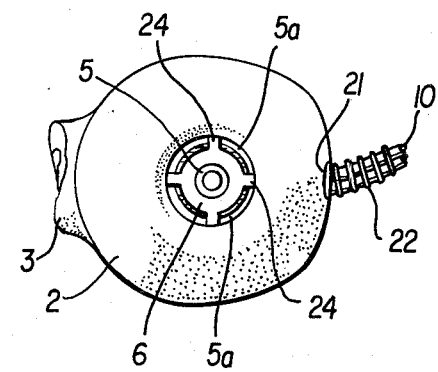
FIG. 4 is a top view of the arrangement shown in FIG. 3.

Referring now to FIGS. 3 and 4, a variation of the method for supporting the resistance heating element 4 and the concentric tube 5 that acts as the heated surface from which evaporation of the volatile compounds takes place is shown. In these FIGS. 3 and 4, the components consisting of the combined on-off switch and variable rheostat or thermostat, and the indicator lamp—shown as items 12 and 17 respectively in FIG. 1—are, for the sake of simplicity, not shown; nor is the related wiring.

In FIG. 3, main power leads 10 connect, by means of connectors 23, to the wires that are permanently affixed to the resistor that is the heat-generating element 4. The wire-wound resistance heating element 4 has a concentric bore, the axis of which is vertically oriented in FIG. 3 and through which tube 5, which acts as the heated surface, passes. The upper end of tube 5 is flared and is connected by means of high temperature solder or by means of weldment to the base of funnel 6. Funnel 6 is supported at several points 24 that insert into corresponding holes 25 in the upper portion of the main upper entrance to cavity 2a in main body structure 2. By this type of construction, heat transfer from the heated surface, tube 5, to the main structural body 2, by the path of funnel 6 is minimized, largely because of the gaps 5a between funnel 6 and the walls of the main entrance hole into the cavity of the main structural body 2. The use of the finger-controlled vent hole 21 can give the user control over the temperature and the ratio of fresh air to evaporated volatile compounds inhaled.

Figure 5:
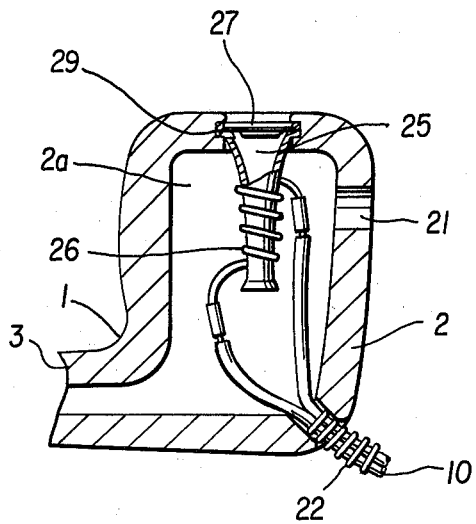
FIG. 5 shows a cross-sectional view of another version of this invention in which the resistance heating element is a heating wire that is wound around the small end of a funnel-shaped glass or ceramic heated surface that is itself supported at its larger end by the main structural body.
Figure 6:
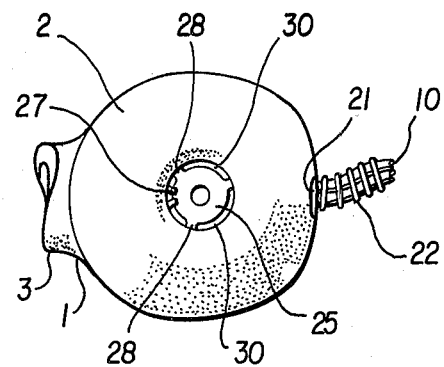
FIG. 6 is a top view of the arrangement shown in FIG. 5.

Referring now to FIGS. 5 and 6, which, as with FIGS. 3 and 4, do not, for simplicity's sake, show the indicator lamp, power controls and related wiring that can be incorporated, show an arrangement in which the heated surface 25 is a funnel made of glass or other ceramic material that has electrical resistance heating wires 26 wound directly around its outer circumference over its norrower lower regions. In this embodiment, the heated surface 25 is held in place in the main structural body 2 by means of a snap ring 27 which, together with several tangs 28 projecting from the larger circumference of the heated surface 25, fit into circumferential groove 29 in the top-most bore in the main structural body 2. The spaces 30 around the upper perimeter of the heated surface 25—i.e., the spaces 30 located between the upper perimeter of heated surface 25 and the inner walls of the top-most bore containing groove 29 in the main structural body 2—minimize the thermal contact between the heated surface 25 and the main body structure 2. Vent hole 21, which can be occluded to varying degrees by the user's finger can be used to modulate the temperature and concentration of vapors that the user receives in his mouth.

Figure 7:
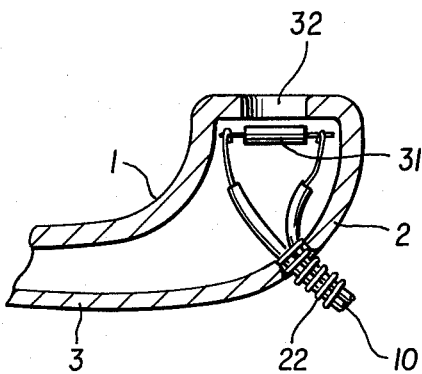
FIG. 7 is a cross-sectional schematic view of a version in which the heated surface is simply an electrical resistor suspended in the entering air passage of the main structural body.

FIG. 7 is a schematic diagram in which the heated surface and the resistance heating element are one and the same electrical resistor 31, having circular, square, or any convenient cross-sectional shape, and situated near the bottom of the main bore opening 34 of the main structural body 2.

Figure 8:
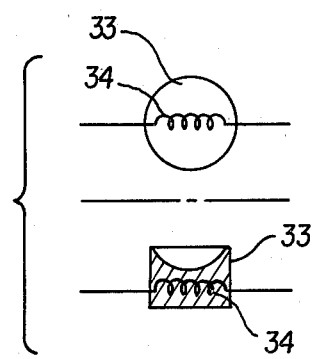
FIG. 8 shows top and side view of a heated surface that is a small glass or ceramic bowl in which the electrical resistance heating wire is embedded.

FIG. 8 is a schematic diagram in top and cut-away side views showing a bowl-shaped glass or ceramic heated surface 33 in which the resistance heating element 34 is directly embedded. This heated surface arrangement shown schematically in FIG. 8 could be supported in a main body structure such as the one shown in FIG. 7, said heated surface 33 being used in place of electrical resistor 31 in FIG. 7.

The foregoing examples and embodiments are merely illustrative of the invention which is to be limited only by the following claims.

What is claimed is:

1. A device for inhaling a mixture of air and vaporized volatile compounds, but without combustion or thermal degradation and pyrolysis of the volatile compounds, for the purpose of the enjoyment of flavor constituents of tobacco and the volatile ingredients of other smoking materials and for the systemic administration, by means of the respiratory route, of synthetic and natural medications that have a vapor pressure of 1 atmosphere at temperatures not greater than 250° C., the device comprising:

a main structural body shaped to be held comfortably in the hand of the user and having a cavity therein and including a mouthpiece and stem that communicates with said cavity;

a heat-generating electrical resistance element suspended in the cavity of said main structural body and out of direct contact with the walls of said cavity;

a surface to be heated in direct thermal contact with said heat-generating electrical resistance element and in indirect thermal contact, and direct mechanical contact, with said main structural body;

a funnel which receives the volatile compounds to be evaporated and directs the flow of said volatile compounds while in their liquid state into the central portion of said surface, and which mechanically connects said surface with the main structural body and thereby supports the surface in the cavity of said main structural body;

air passages communicating with the stem and mouthpiece portions of said main structural body and so arranged that the air that moves through the device may entrain the vapors of the evaporated volatile compounds so that a mixture of air and vaporized volatile compounds can be inhaled through the mouthpiece portion of said main structural body;

a vent hole bored substantially horizontally into the cavity of said main structural body, said vent hole being conveniently placed so that the user of the invention may partially or totally cover said vent hole with a finger or other portion of the hand and thereby effect control over the ratio of air to evaporated volatile compounds thence inhaled through the mouthpiece portion of said main structural body;

a combined on-off switch and variable power control mechanism whereby the user of the invention can adjust the temperature of the surface, said combined switch and control mechanism being conveniently and aesthetically attached to and projected through and into the cavity of said main structural body in such a way that the electrical wires that connect with said combined switch and control mechanism will be connected with the combined switch and control mechanism inside of said cavity, while the portions of the combined switch and control that are to be manipulated by the user of the invention project beyond the outer surface of said main structural body;

an indicator lamp contained within the main structural body, but so located as to be easily visible to the user, said indicator lamp serving the function of indicating to the user of the invention that the heat-generating electrical resistance element is receiving electrical power and thereby generating heat for said heated surface; and a double-wire power cord that projects through a hole in the main structural body and connects, inside of the cavity of said main structural body, with the heat-generating electrical resistance element, the indicator lamp, and with the combined on-off switch and power control mechanism, and which at its extreme end away from the main structural body, has a plug means for connection with an electrical power source.

* * * * *